US008417317B2

(12) United States Patent
Kabasawa

(10) Patent No.: US 8,417,317 B2
(45) Date of Patent: Apr. 9, 2013

(54) BLOOD FLOW DYNAMIC ANALYSIS APPARATUS AND METHOD, AND MAGNETIC RESONANCE IMAGING SYSTEM

(75) Inventor: Hiroyuki Kabasawa, Tokyo (JP)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 453 days.

(21) Appl. No.: 12/607,003

(22) Filed: Oct. 27, 2009

(65) Prior Publication Data

US 2010/0113914 A1 May 6, 2010

(30) Foreign Application Priority Data

Oct. 31, 2008 (JP) ................................ 2008-281511

(51) Int. Cl.
*A61B 5/05* (2006.01)
(52) U.S. Cl.
USPC ............ 600/420; 600/419; 382/128; 424/9.1
(58) Field of Classification Search .................. 600/410, 600/419, 420, 431–435; 382/128, 286, 291, 382/282, 308; 424/9.1, 9.3
See application file for complete search history.

(56) References Cited

U.S. PATENT DOCUMENTS

| | | | |
|---|---|---|---|
| 5,590,654 A | 1/1997 | Prince | |
| 5,853,370 A | 12/1998 | Chance et al. | |
| 6,230,041 B1 | 5/2001 | Prince | |
| 6,542,769 B2 * | 4/2003 | Schwamm et al. | 600/420 |
| 7,069,068 B1 | 6/2006 | Ostergaard | |
| 7,333,845 B2 * | 2/2008 | Hundley et al. | 600/407 |
| 2004/0010180 A1 | 1/2004 | Scorvo | |
| 2004/0059183 A1 | 3/2004 | Jansen et al. | |
| 2004/0167375 A1 | 8/2004 | Couvillon, Jr. | |
| 2005/0148814 A1 | 7/2005 | Fischi et al. | |
| 2006/0211909 A1 | 9/2006 | Anstadt et al. | |

FOREIGN PATENT DOCUMENTS

JP 2006-326078 12/2006

* cited by examiner

*Primary Examiner* — Parikha Mehta
(74) *Attorney, Agent, or Firm* — Armstrong Teasdale LLP

(57) ABSTRACT

A blood flow dynamic analysis apparatus acquires data from a plurality of regions lying in slices set to a subject with a contrast agent injected therein and analyzes blood flow dynamics of the subject, based on the data. The apparatus includes a contrast agent concentration profile generation device for generating profiles each indicative of a temporal change in the concentration of the contrast agent for every said region lying in the slices, a characteristic amount calculation device for calculating the concentrations of the contrast agent in the regions after a bolus of contrast agent has passed through the regions, from the profiles, a histogram generation device for generating a histogram containing the concentrations of the contrast agent in the regions after the bolus of contrast agent has passed through the regions, a region determination device for determining a region in which each vein exists, from the regions, based on the histogram, and a function calculation device for calculating a venous output function, based on a temporal change in the concentration of the contrast agent in the region in which the vein exists.

20 Claims, 16 Drawing Sheets

MAP OF PEAK CONCENTRATION (Cmax)

MAP OF PEAK CONCENTRATION ACHIEVED TIME TTP

MAP OF POST-BOLUS PASSAGE CONCENTRATION Cp

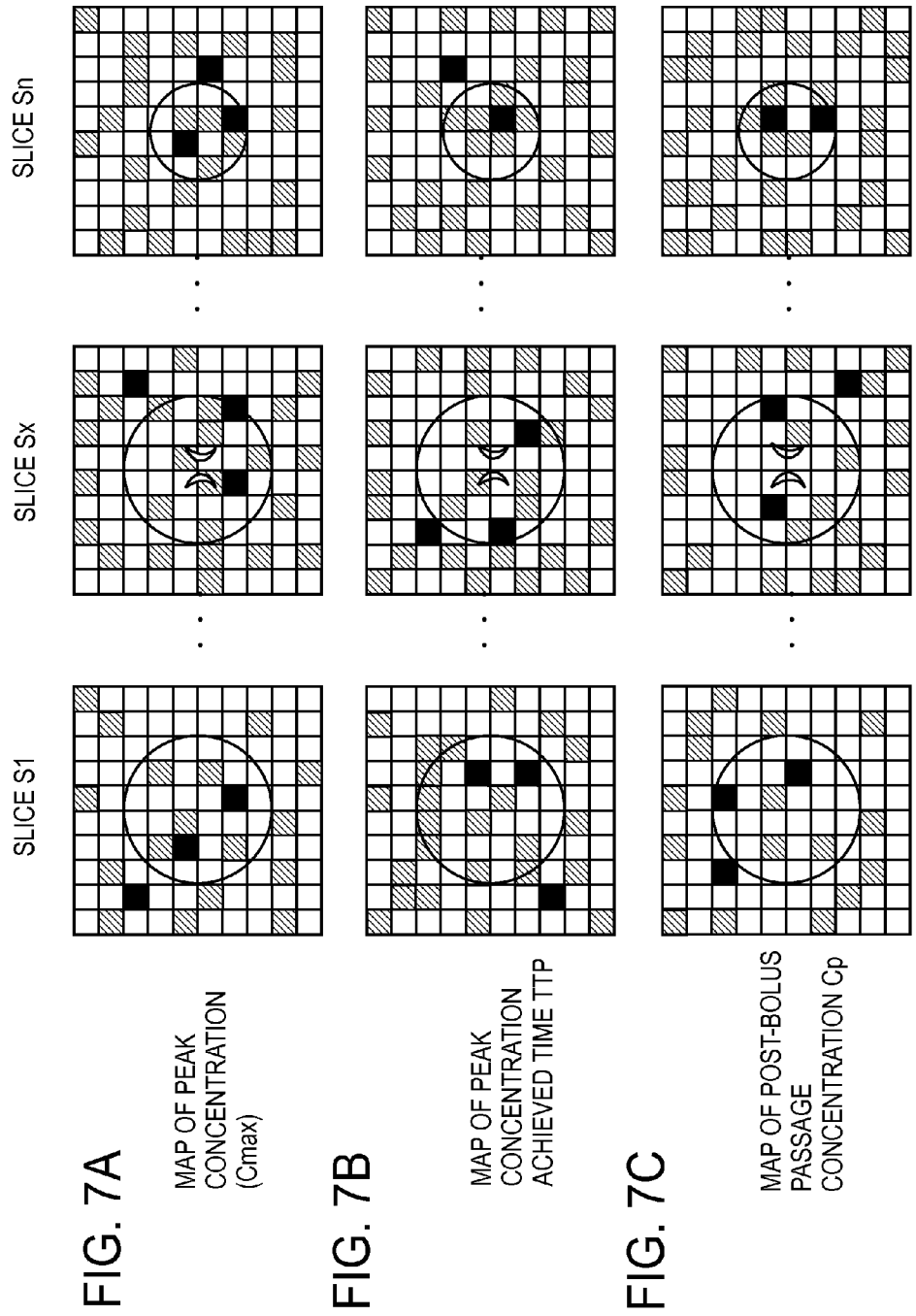

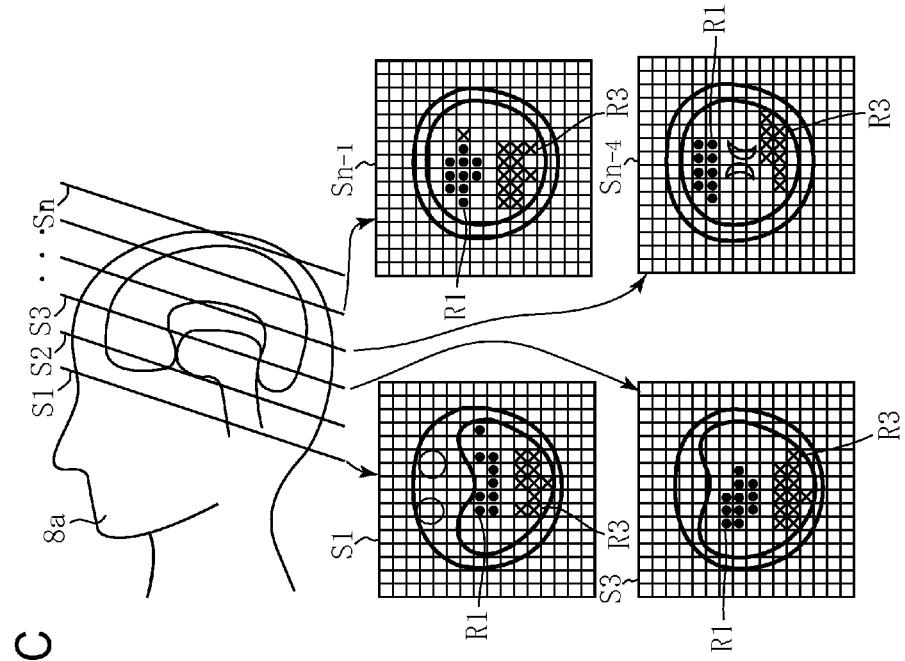
FIG. 13A
FIG. 13B
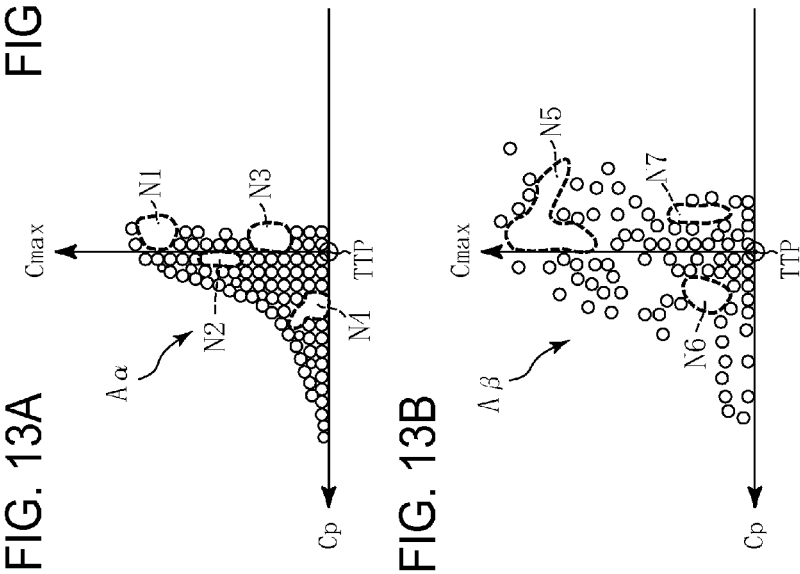
FIG. 13C

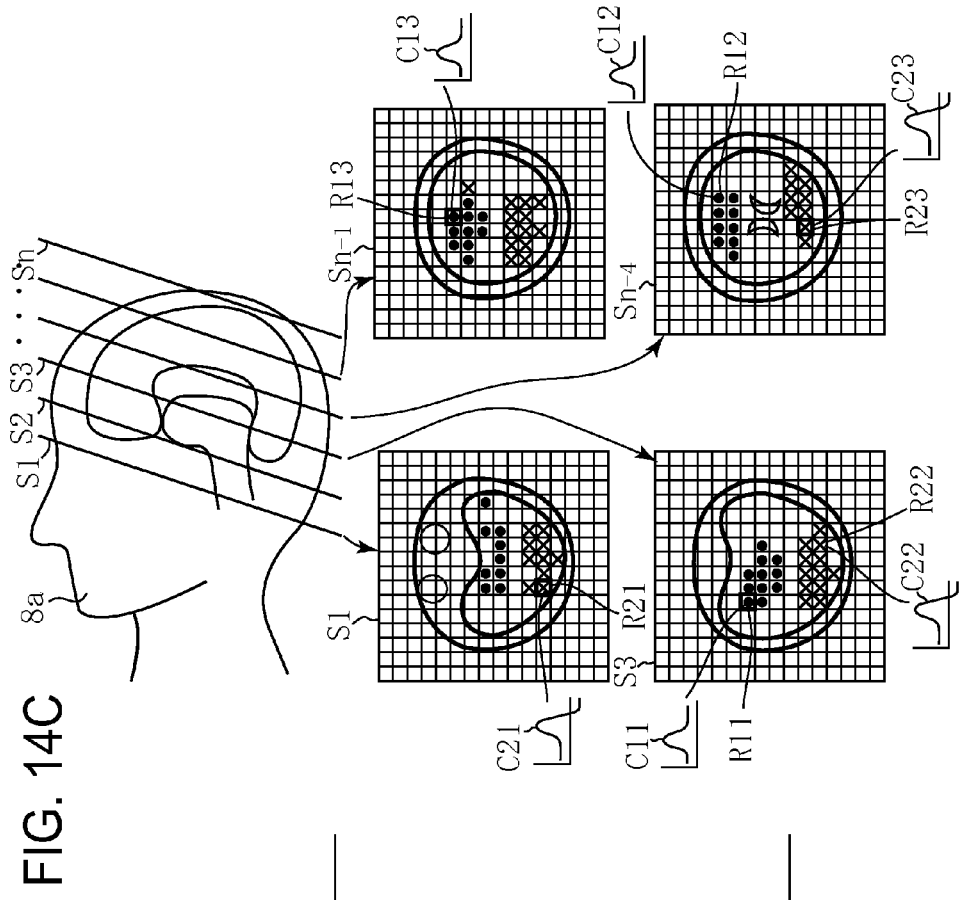
FIG. 14C
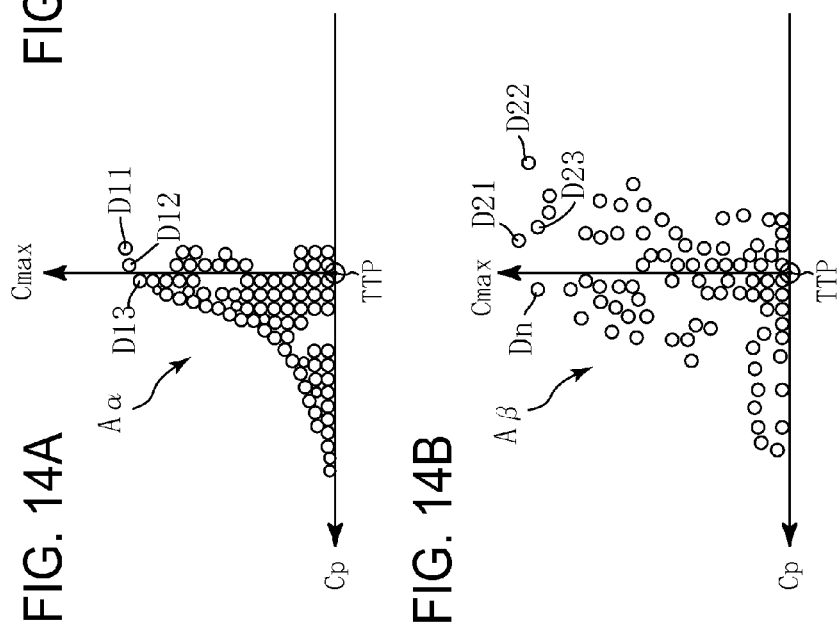
FIG. 14A
FIG. 14B

BLOOD FLOW DYNAMIC ANALYSIS APPARATUS AND METHOD, AND MAGNETIC RESONANCE IMAGING SYSTEM

CROSS REFERENCE TO RELATED APPLICATIONS

This application claims the benefit of Japanese Patent Application No. 2008-281511 filed Oct. 31, 2009, which is hereby incorporated by reference in its entirety.

BACKGROUND OF THE INVENTION

The embodiments described herein relate to a blood flow dynamic analysis apparatus and method for analyzing blood flow dynamics of a subject, and a magnetic resonance imaging system having the blood flow dynamic analysis apparatus.

BACKGROUND ART

There is a need to perform suitable treatment on a patient having caused cerebral infarction quickly. The important of quantifying a blood flow state of the brain of a subject is rising to perform the prompt treatment. Therefore, there have been proposed various methods for conducting computerized tomographic scanning of the brain of the subject using a contrast agent and quantifying a blood flow state of its brain (refer to Japanese Unexamined Patent Publication No. 2006-326078).

There is a need to calculate an arterial input function (AIF) and a venous output function (VOF) where a blood flow state of a brain is quantified. The arterial input function is of a function calculated from a temporal change in the concentration of a contrast agent in an artery of a subject's tomographic image. The venous output function is of a function calculated from a temporary change in the concentration of the contract agent in a vein of the subject's tomographic image. When, however, the inner diameter of the artery of the subject's brain becomes narrow due to causes such as a focus, the temporal change in the concentration of the contrast agent in the artery might exhibit a behavior similar to the temporal change in the concentration of the contrast agent in the vein. In this case, a conventional method might calculate the venous output function, based on the temporary change in the concentration of the contrast agent in the artery, thus encountering difficulties in calculating the accurate venous output function.

BRIEF DESCRIPTION OF THE INVENTION

Embodiments include a blood flow dynamic analysis apparatus for acquiring data from a plurality of regions lying in slices set to a subject with a contrast agent injected therein and analyzing blood flow dynamics of the subject, based on the data, including: a contrast agent concentration profile generation device for generating profiles each indicative of a temporal change in the concentration of the contrast agent for every region lying in the slices, a characteristic amount calculation device for calculating the concentrations of the contrast agent in the regions after a bolus of contrast agent has passed through the regions, from the profiles, a histogram generation device for generating a histogram containing the concentrations of the contrast agent in the regions after the bolus of contrast agent has passed though the regions, a region determination device for determining a region in which each vein exists, from the regions, based on the histogram, and an output function calculation device for calculating a venous output function, based on a temporal change in the concentration of the contrast agent in the region in which the vein exists.

In some embodiments, the concentration of a contrast agent after the passage of a bolus of contrast agent is calculated for every region lying in slices from a contrast agent concentration profile generated for every region lying in each slice. The concentration of the contrast agent after the passage of the bolus of contrast agent has a tendency to assume values different depending on whether the bolus of contrast agent flows through an artery or a vein. Thus, a vein-containing region and an artery-containing region can be distinguished from each other within each slice by generating a histogram containing the concentrations of the contrast agent after the bolus of contrast agent has passed, thus making it possible to calculate a more accurate venous output function.

Further objects and advantages of the present invention will be apparent from the following description of the preferred embodiments of the invention as illustrated in the accompanying drawings.

BRIEF DESCRIPTION OF THE DRAWINGS

FIGS. 7A, 7B, and 7C are diagrams schematically showing three maps (map of peak concentration Cmax, map of peak concentration achieved time TTP, and map of concentration Cp after passage of bolus) of the respective slices S1 through Sn.

FIGS. 13A, 13B, and 13C are diagrams showing the manner after dots have been eliminated from ranges N1 through N7 of the joint histogram.

FIGS. 14A, 14B, and 14C are diagrams showing which region R is selected from regions R left within the head 8a of the subject 8 with the respective slices S1 through Sn set thereto.

DETAILED DESCRIPTION OF THE INVENTION

Figure 1:
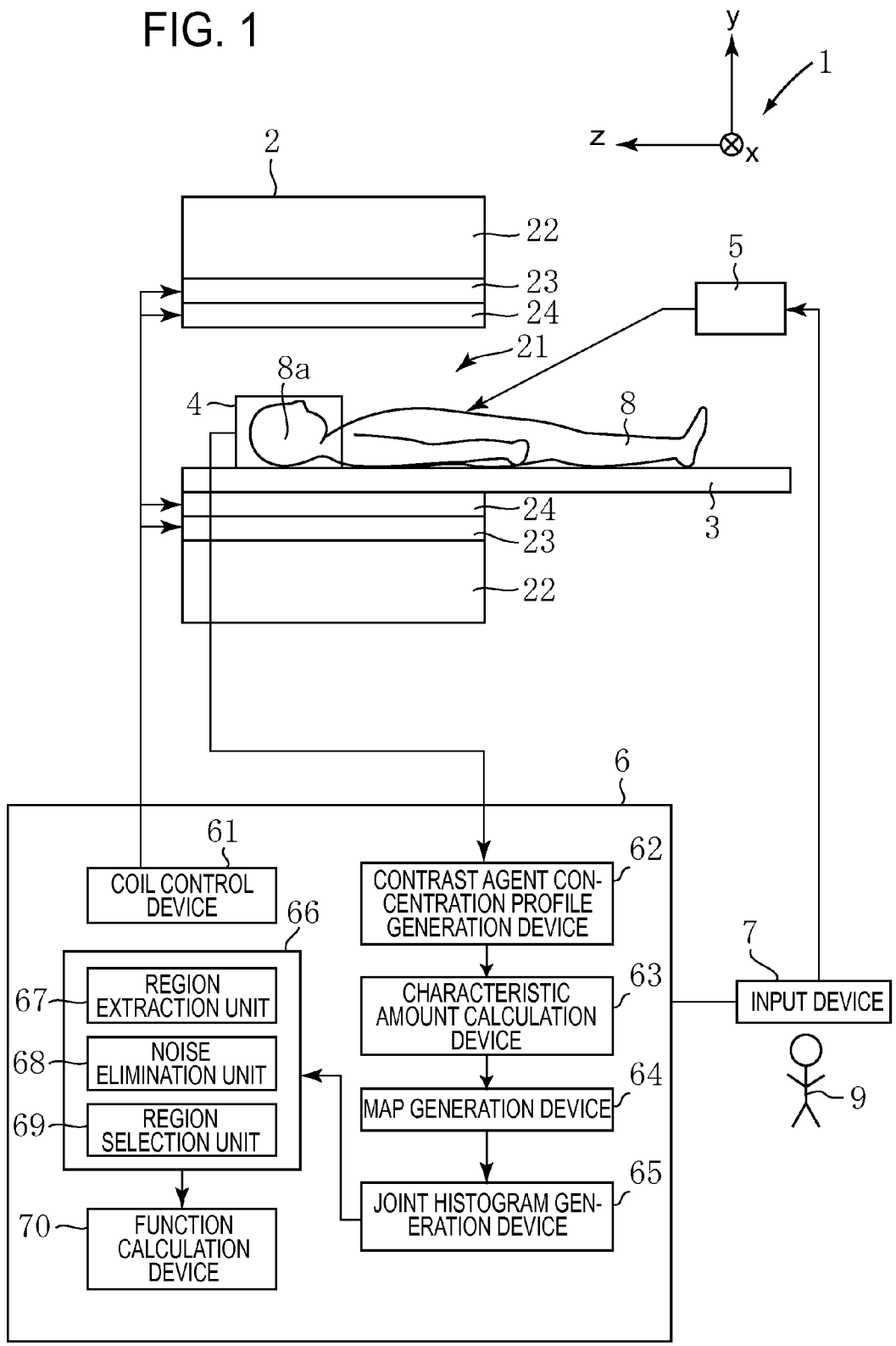
FIG. 1 is a schematic diagram of a magnetic resonance imaging system 1 according to one embodiment of the invention.

FIG. 1 is a schematic diagram of a magnetic resonance imaging system 1 according to one embodiment of the invention.

The magnetic resonance imaging system (hereinafter called "MRI (Magnetic Resonance Imaging) system") 1 has a gantry 2, a cradle 3, a receiving coil 4, a contrast agent injecting device 5, a controller 6 and an input device 7.

The gantry 2 has a bore 21 in which a subject 8 is accommodated, a superconductive coil 22, a gradient coil 23 and a transmitting coil 24. The superconductive coil 22 generates a static magnetic field BO, the gradient coil 23 applies a gradient pulse and the transmitting coil 24 transmits an RF pulse.

The cradle 3 is configured so as to move in a z direction and a −z direction. With the movement of the cradle 3 in the z direction, the subject 8 is conveyed to the bore 21. With the movement of the cradle 3 in the −z direction, the subject 8 conveyed to the bore 21 is carried out of the bore 21.

The contrast agent injecting device 5 injects a contrast agent to the subject 8.

The receiving coil 4 is attached to the head 8a of the subject 8. An MR (Magnetic Resonance) signal received by the receiving coil 4 is transmitted to the controller 6.

The controller 6 has a coil control device 61 through a function calculation device 70.

The coil control device 61 controls the transmitting coil 24 and the gradient coil 23 in response to an imaging command of the subject 8 inputted from the input device 7 by an operator 9 in such a manner that a pulse sequence for imaging the subject 8 is executed.

Figure 5A:
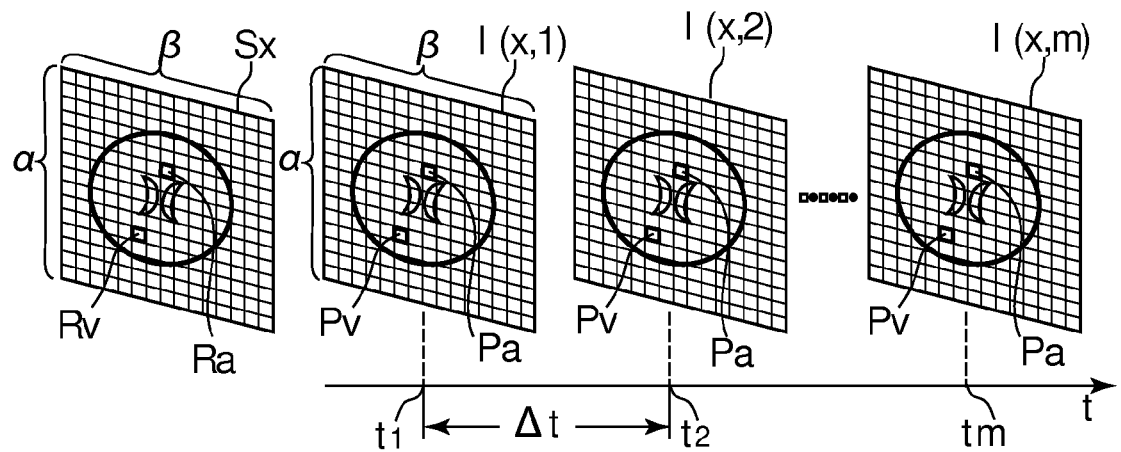
FIGS. 5A, 5B, and 5C are diagrams showing a method for calculating temporal changes in the concentration of a contrast agent in a sectional area of a slice Sx set to the head 8a of the subject 8.

The contrast agent concentration profile generation device 62 calculates contrast agent concentration-time curves Ga and Gv each indicative of a temporal change in the concentration of the contrast agent of the head 8a of the subject 8 in every region of slices S1 through Sn (refer to FIG. 5A).

The characteristic amount calculation device 63 calculates three characteristic amounts (peak concentration Cmax, peak concentration achieved time TTP and concentration Cp after the passage of bolus) of the contrast agent concentration-time curves Ga and Gv (refer to FIGS. 5B and 5C)).

The map generation device 64 generates a map of a peak concentration Cmax, a map of a peak concentration achieved time TTP and a map of a concentration Cp after the bolus passage with respect to each of the slices S1 through Sn (refer to FIGS. 6A-6C and 7A-7C).

The joint histogram generation device 65 generates a joint histogram (refer to FIG. 8) for a peak concentration Cmax, a peak concentration achieved time TTp and a concentration Cp after the passage of a bolus, from the maps of the peak concentrations Cmax, the maps of the peak concentration achieved times TTP and the maps of the concentrations Cp after the bolus passage each map obtained for each of the slices S1 through Sn (refer to FIG. 7A-7C).

Figure 8:
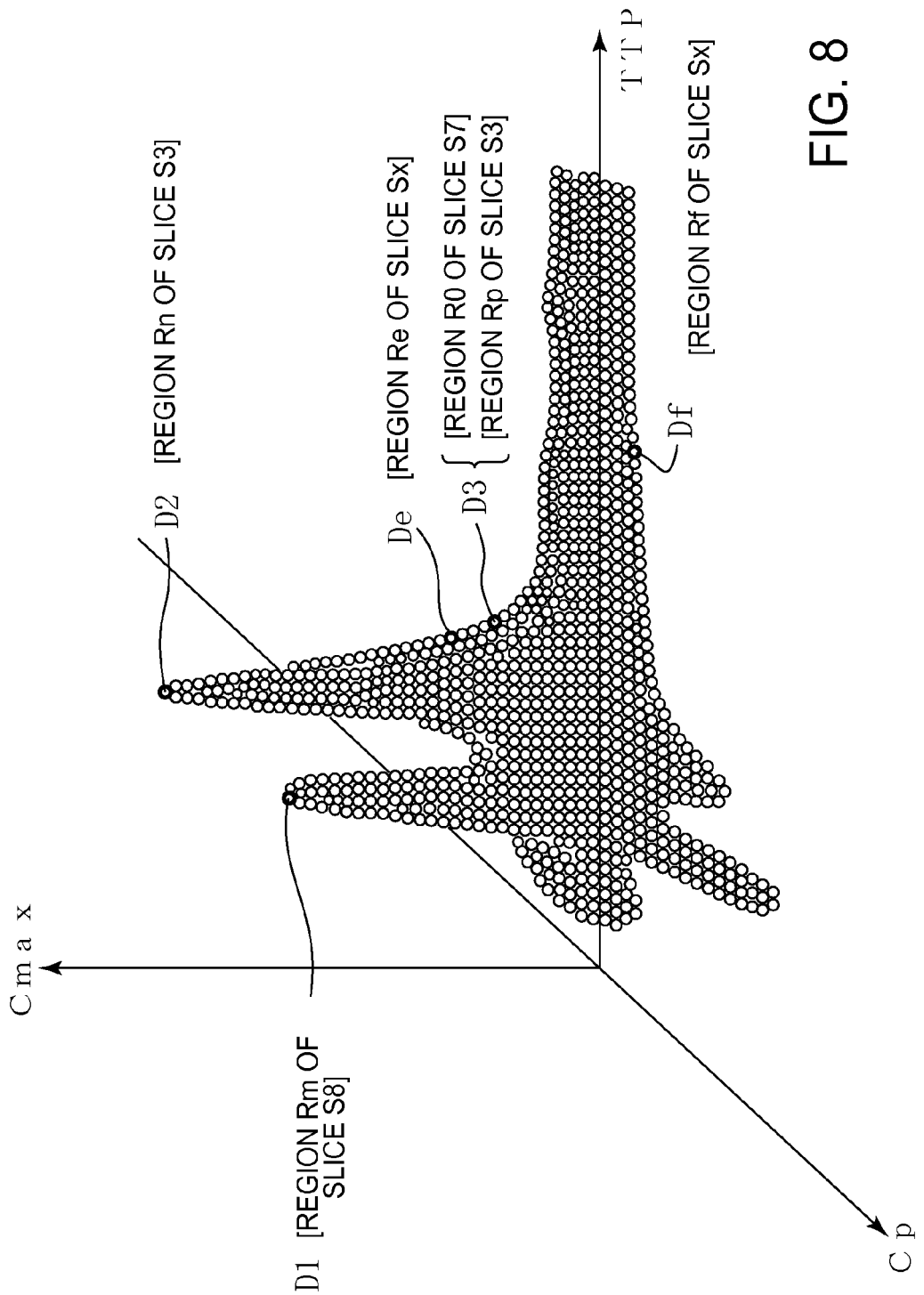
FIG. 8 is a diagram schematically showing one example of a joint histogram.

The region determination device 66 determines a region in which each vein exists and a region in which each artery exists, from all regions R contained in the slices S1 through Sn, based on the joint histogram (refer to FIG. 8). The region determination device 66 has a region extraction unit 67, a noise elimination unit 68 and a region selection unit 69.

The region extraction unit 67 extracts a plurality of regions R1 and R2 (refer to FIG. 12C) each having a peak concentration achieved time (refer to FIG. 11) lying within a range from t1 to t2 and a plurality of regions R3 and R4 (refer to FIG. 12C) each having a peak concentration achieved time (refer to FIG. 11) lying within a range from t3 to t4, from all the regions R contained in the slices S1 through Sn.

Figures 12A, 12B, 12C:
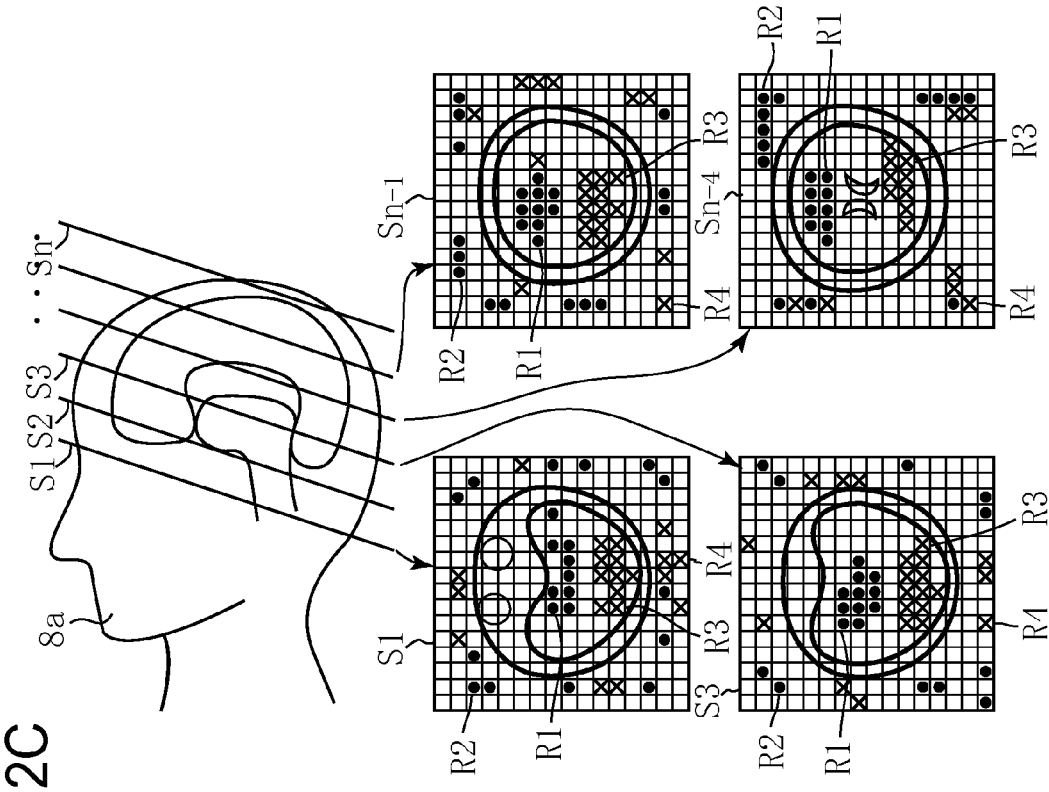
FIGS. 12A, 12B, and 12C are diagrams showing drawings each projected onto a Cmax-Cp surface.

The noise elimination unit 68 eliminates the regions R2 indicative of noise from the regions R1 and R2 (refer to FIG. 12C) and eliminates the regions R4 indicative of noise from the regions R3 and R4 (refer to FIG. 12C).

The region selection unit 69 selects regions R11, R12 and R13 (refer to FIG. 14C) in which the arteries exist, from the plural regions R1, based on the post-bolus passage concentration Cp. Further, the region selection unit 69 selects regions R21, R22 and R23 (refer to FIG. 14C) in which the veins exist, from the plural regions R3, based on the post-bolus passage concentration Cp.

Figure 16:
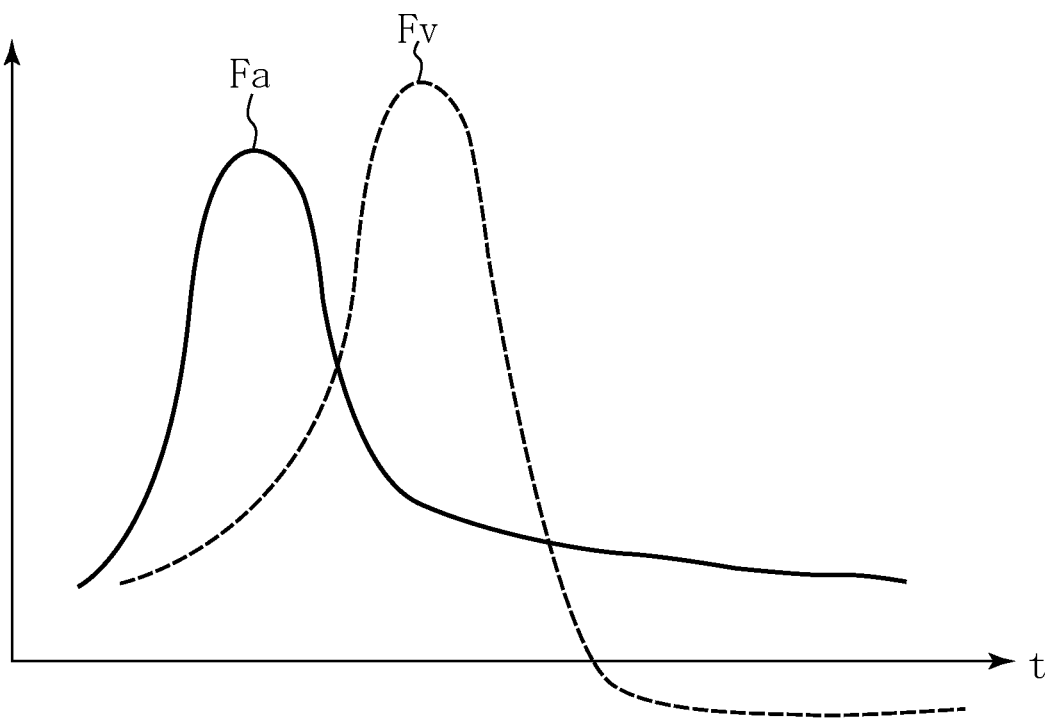
FIG. 16 is a diagram showing an arterial input function and a venous output function both calculated.

The function calculation device 70 adds and averages contrast agent concentration-time curves C11, C12 and C13 in the selected three regions R11, R12 and R13 thereby to calculate an arterial input function Fa (refer to FIG. 16). Further, the function calculation device 70 adds and averages contrast agent concentration-time curves C21, C22 and C23 in the selected three regions R21, R22 and R23 thereby to calculate a venous output function Fv (refer to FIG. 16).

The input device 7 inputs various commands to the controller 6 according to the operation of the operator 9.

Figure 2:
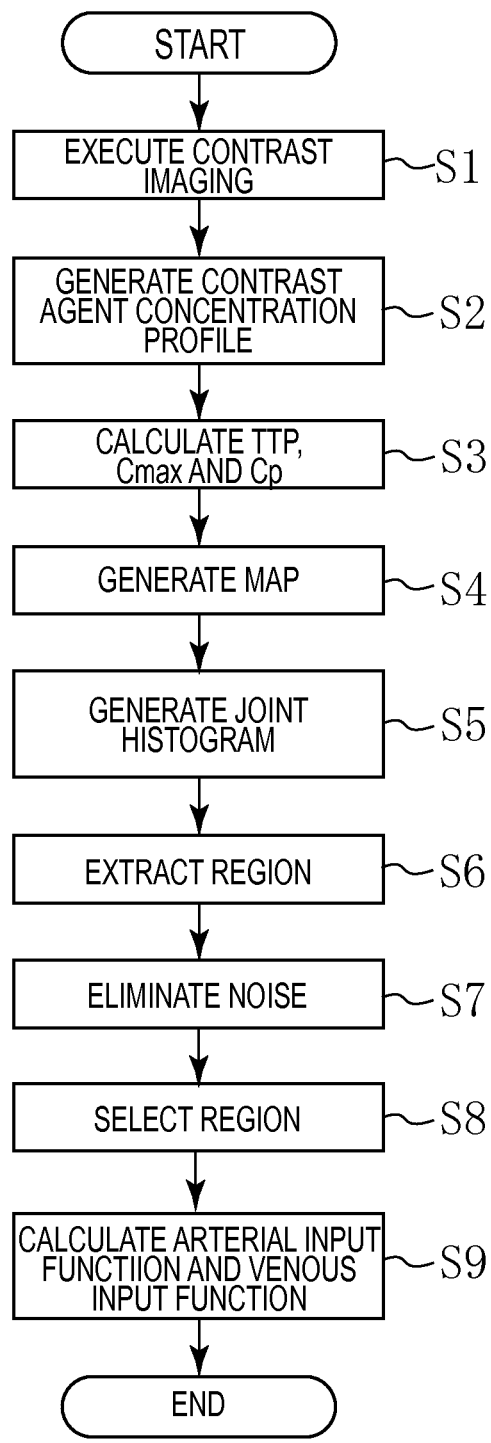
FIG. 2 is a diagram showing a processing flow of the magnetic resonance imaging system 1.

FIG. 2 is a diagram showing a processing flow of the magnetic resonance imaging system 1.

At Step S1, contrast imaging for the head 8a of the subject 8 is carried out. The operator operates the input device 7 to set each slice to the subject 8.

Figure 3:
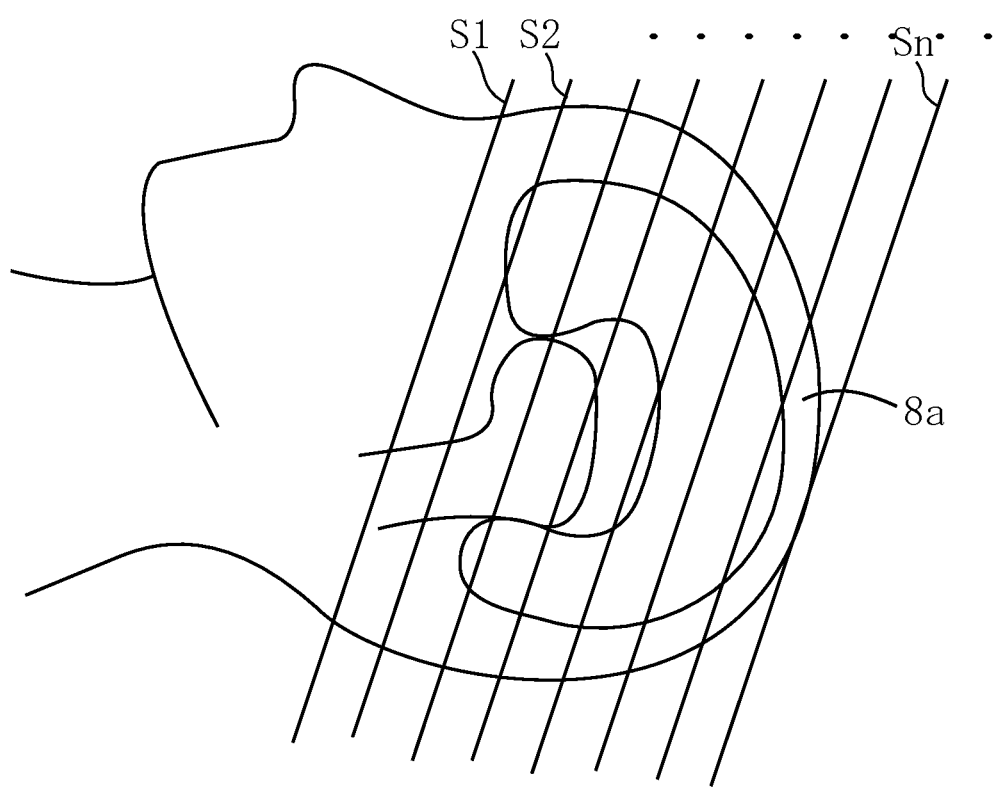
FIG. 3 is one example illustrative of slices set to a subject 8.

FIG. 3 is one example illustrative of slices set to the subject 8.

In the subject 8, n slices S1 through Sn are set. The number of slices is n=12, for example. The number of slices can be set to an arbitrary number of slices as needed. Imaging regions for the head 8a of the subject 8 are determined for each of the slices S1 through Sn.

After the slices S1 through Sn have been set, the operator 9 transmits a contrast agent injection command to the contrast agent injecting device 5 and transmits an imaging command for imaging the subject 8 to the coil control device 61 of the MRI system (refer to FIG. 1). The coil control device 61 controls the transmitting coil 24 and the gradient coil 23 in response to the imaging command in such a manner that a pulse sequence for imaging the head 8a of the subject 8 is executed.

In the present embodiment, a pulse sequence for obtaining continuously-imaged or shot m images from respective slices by multi-slice scan is executed. Thus, the m images are obtained per slice. For example, the number of images m=85. Data are acquired from the head 8a of the subject 8 by executing the pulse sequence.

Figure 4:
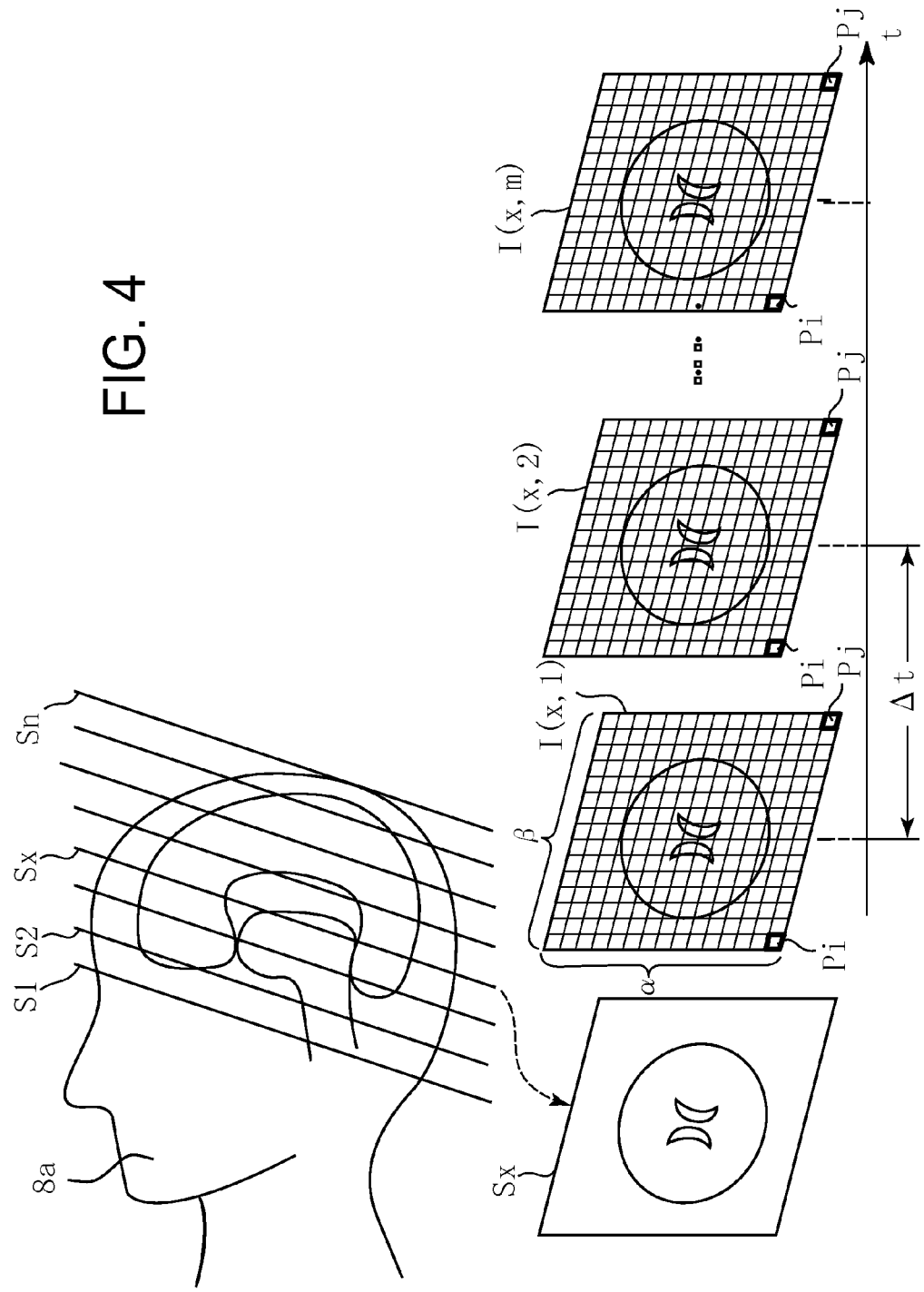
FIG. 4 is a conceptual diagram showing images obtained from a slice Sx of slices S1 through Sn.

FIG. 4 is a conceptual diagram showing images obtained from the slice Sx of the slices S1 through Sn.

m images I (x, 1) through I (x, m) are obtained from the section of the slice Sx. The respective images I (x, 1) through I (x, m) have α×β pieces of pixels P. The positions of two pixels Pi and Pj in each of the images I (x, 1) through I (x, m) are illustrated in FIG. 4.

Incidentally, although only the images obtained from the slice Sx are shown in FIG. 4, m images are obtained even from other slices in a manner similar to the slice Sx.

After the execution of Step S1, the processing flow proceeds to Step S2.

At Step S2, the contrast agent concentration profile generation device 62 (refer to FIG. 1) calculates temporal changes in the concentration of the contrast agent of the head 8a of the subject 8 in sectional areas of the slices S1 through Sn. Referring to FIG. 5, a description will be made below of how the contrast agent concentration profile generation device 62 calculates the temporal changes in the concentration of the contrast agent.

Figure 5B:
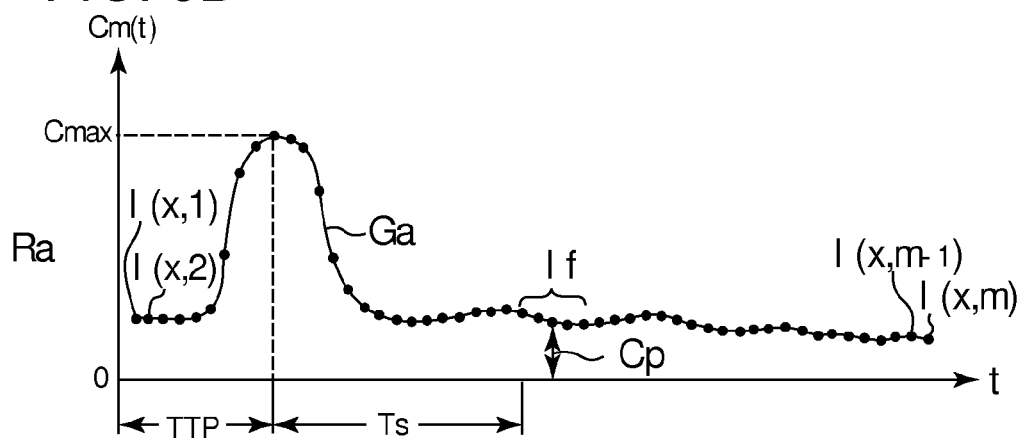
Figure 5C:
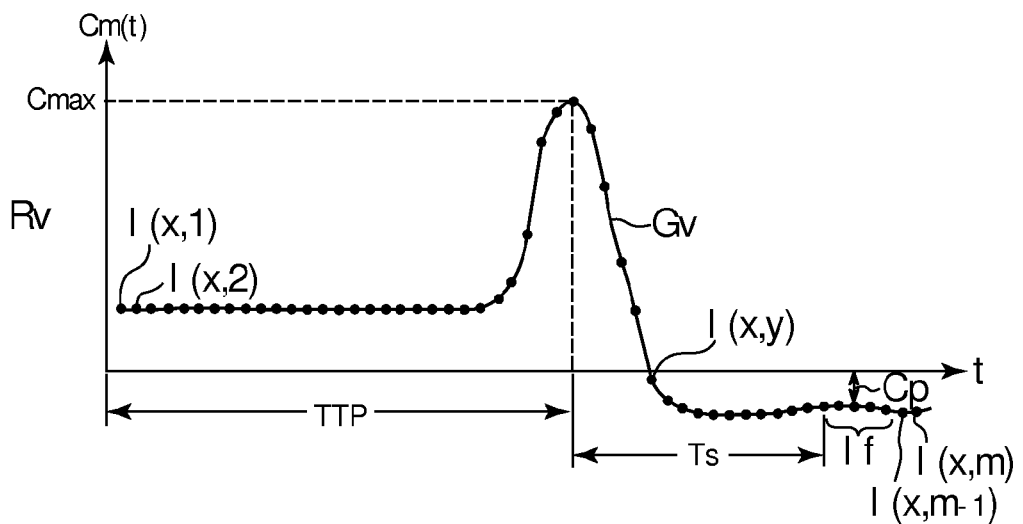

FIGS. 5A, 5B, and 5C are diagrams showing a method for calculating a temporal change in the concentration of the contrast agent in the sectional area of the slice Sx set to the head 8a of the subject 8.

The section (refer to FIG. 4) of the slice Sx of the subject 8 and the images I (x, 1) through I (x, m) of the slice Sx are shown in FIG. 5A. The respective images I (x, 1) through I (x, m) are images of the slice Sx at times t1, t2, ..., tm (time interval Δt).

The section of the slice Sx is divided into α×β pieces of regions R. The positions of two regions Ra and Rv in the section of the slice Sx are specifically shown in FIG. 5A. The region Ra is a region including each artery, whereas the region Rv is a region including each vein. Respective pixels P of the images I (x, 1) through I (x, m) are those obtained by imaging the respective regions R of the slice Sx at the times t1, t2, ..., tm. For example, the respective pixels Pa of the images I (x, 1) through I (x, m) are those obtained by imaging the region Ra of the slice Sx at the times t1, t2, ..., tm. The pixels Pv of the images I (x, 1) through I (x, m) are those obtained by imaging the region Rv of the slice Sx at the times t1, t2, ..., tm.

A schematic diagram of the contrast agent concentration-time curve (contrast agent concentration profile) Ga in the region Ra of the slice Sx is shown in FIG. 5B. The horizontal axis indicates the time t, and the vertical axis indicates a concentration value Cm (t) of the contrast agent in the region Ra of the slice Sx. In FIG. 5B, the imaging start time of the slice Sx is defined to be t=0. The contrast agent concentration-time curve Ga is generated by connecting plots of the concentration values Cm (t) of the contrast agent at the pixels Pa of the images I(x, 1) through I(x, m) to one another in lines.

A schematic diagram of the contrast agent concentration-time curve (contrast agent concentration profile) Gv in the region Rv of the slice Sx is shown in FIG. 5C. The horizontal axis indicates the time t, and the vertical axis indicates a concentration value Cm (t) of the contrast agent in the region Rv of the slice Sx. Even in FIG. 5C, the imaging start time of the slice Sx is defined to be t=0 in a manner similar to FIG. 5B. The contrast agent concentration-time curve Gv is generated by connecting plots of the concentration values Cm (t) of the contrast agent at the pixels Pv of the images I(x, 1) through I(x, m) to one another in lines.

In the contrast agent concentration-time curve Ga (refer to FIG. 5B) in the region Ra including the artery, the concentration Cm (t) of the contrast agent is positive in value even at any of the images I (x, 1) through I (x, m). In the contrast agent concentration-time curve Gv (refer to FIG. 5C) in the region Rv including the vein, however, the concentration Cm (t) of the contrast agent is negative in value in the images I (x, 1) through I (x, m). In general, it is known experimentally that when the concentrations Cm (t) of the contrast agent are respectively calculated based on the data of the images (x, 1) through I (x, m) acquired at the MRI system, there is a tendency that the concentrations Cm (t) of the contrast agent are calculated as positive values in the region Ra containing the artery, whereas there is a tendency that the concentrations Cm (t) of the contrast agent at the images I (x, y) through I (x, m) acquired at late times are calculated as negative values in the region Rv containing the vein.

Although the contrast agent concentration-time curves in the two regions Ra and Rv of the slice Sx are shown in FIGS. 5A-5C, the contrast agent concentration-time curves are generated even in other regions in the slice Sx. Further, the contrast agent concentration-time curves are generated similarly even in respective regions of other slices other than the slice Sx.

After the contrast agent concentration-time curves have been generated, the processing flow proceeds to Step S3.

At Step S3, the characteristic amount calculation device 63 calculates the characteristic amounts of the contrast agent concentration-time curves Ga and Gv (refer to FIGS. 5B and 5C). In the present embodiment, the three characteristic amounts (peak concentration Cmax, peak concentration achieved time TTP and post-bolus passage concentration Cp) are calculated as the characteristic amounts of the contrast agent concentration-time curves Ga and Gv as shown in FIGS. 5B and 5C.

The peak concentration Cmax indicates the peak value of the concentration Cm (t) of the contrast agent.

The peak concentration achieved time TTP indicates the time from the imaging start time (t=0) to the time at which the concentration reaches the peak concentration Cmax. However, the start time for the peak concentration achieved time TTP can also be set to other times (for example, time at which the contrast agent is administrated).

The post-bolus passage concentration Cp indicates the concentration of the contrast agent after the bolus of contrast agent has passed through each of the regions R of the slices. In the present embodiment, the time at which the bolus of contrast agent has passed through each region R is set to the time at which a predetermined time Ts has elapsed from the time at which the concentration has reached the peak concentration Cmax. The predetermined time Ts is of an experimentally determinable value and can be set to, for example, a value ranging from about 5 to 10 seconds. However, this time may be suitably determined according to the type of contrast agent and other conditions. In the present embodiment as well, the post-bolus passage concentration Cp is taken as the average value of the concentrations Cm (t) of the contrast agent at a plurality of (for example, five) images If after the predetermined time Ts has elapsed. However, the concentration Cm (t) of the contrast agent at one image lying immediately after the predetermined time Ts has elapsed may be defined as the post-bolus passage concentration Cp.

The peak concentration Cmax (refer to FIG. 5C) in the region Rv containing the vein has a characteristic that appears with being delayed in time more than at the peak concentration Cmax (refer to FIG. 5B) in the region Ra containing the artery. Since the concentration Cm (t) of the contrast agent has the tendency to be calculated as the positive value in the region Ra containing the artery as described above, the post-bolus passage concentration Cp in the region Ra containing the artery also has a tendency to be calculated as the positive value (refer to FIG. 5B). Since, however, the concentrations Cm (t) of the contrast agent at the images I (x, y) through I (x, m) acquired at the late times has the tendency to be calculated as the negative values in the region Rv containing the vein, the post-bolus passage concentration Cp in the region Rv containing the vein has a tendency to assume the negative value (refer to FIG. 5C).

Incidentally, although the peak concentrations Cmax, peak concentration achieved times TTP and post-bolus passage concentrations Cp in the two regions Ra and Rv of the slice Sx have been shown in FIGS. 5A-5C, the peak concentrations Cmax, peak concentration achieved times TTP and post-bolus passage concentrations Cp are calculated similarly even with respect to other regions R. Further, the peak concentrations Cmax, peak concentration achieved times TTP and post-bolus passage concentrations Cp are calculated similarly even with respect to the respective regions of the slices other than the slice Sx.

After the peak concentrations Cmax, the peak concentration achieved times TTP and the post-bolus passage concentrations Cp have been calculated as described above, the processing flow proceeds to Step S4.

At Step S4, the map generation device 64 (refer to FIG. 1) generates maps of peak concentrations Cmax, maps of peak concentration achieved times TTP and maps of post-bolus passage concentrations Cp with respect to the slices S1 through Sn (refer to FIGS. 6A-6C and 7A-7C).

Figure 6A:
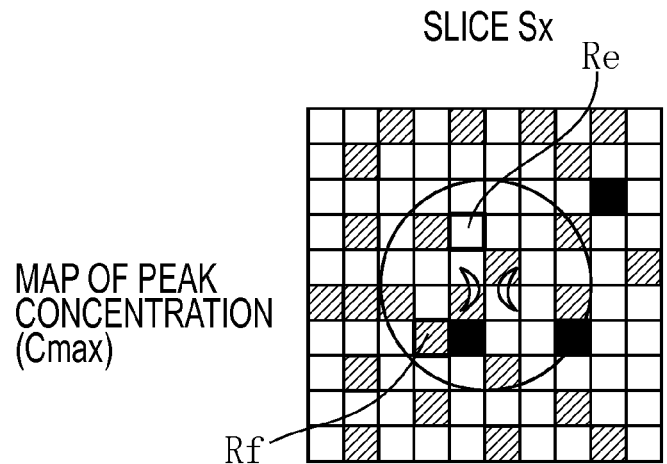
FIGS. 6A, 6B, and 6C are diagrams schematically showing a map of peak concentration Cmax, a map of a peak concentration achieved time TTP and a map of a concentration Cp after passage of a bolus with respect to the slice Sx.
Figure 6B:
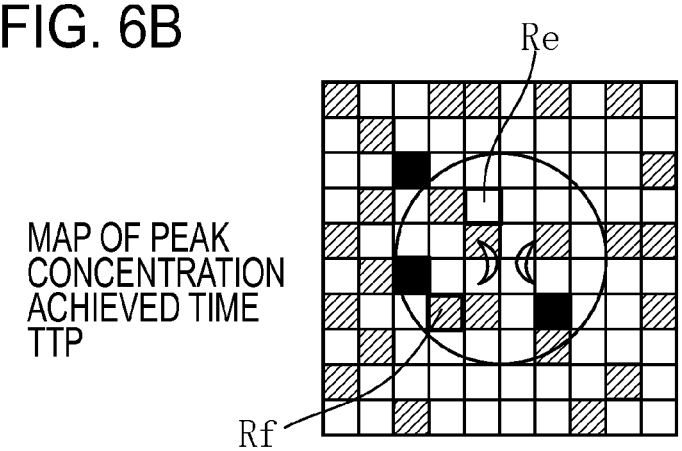
Figure 6C:
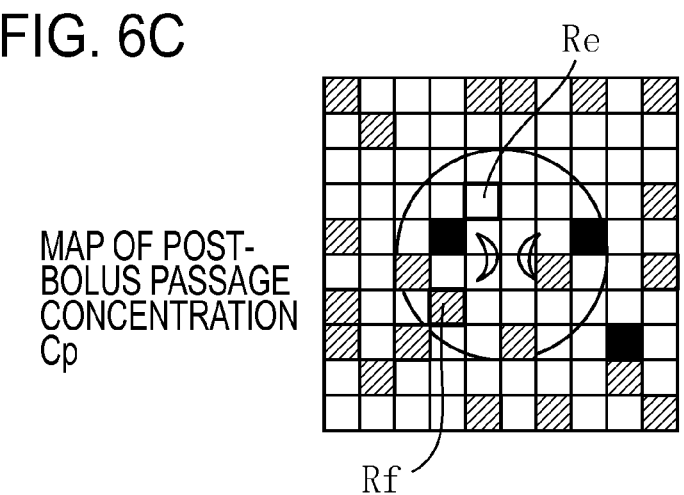

FIGS. 6A, 6B, and 6C are figures schematically showing a map of a peak concentration Cmax, a map of a peak concentration achieved time TTP and a map of a post-bolus passage concentration Cp related to the slice Sx.

FIG. 6A is the map of the peak concentration Cmax about the slice Sx, FIG. 6B is the map of the peak concentration achieved time TTP about the slice Sx, and FIG. 6C is the map of the post-bolus passage concentration Cp about the slice Sx, respectively.

The differences in magnitude between the peak concentrations Cmax related to the regions R lying in the slice Sx are shown in FIG. 6A in the form of shadings of the regions R. The larger the peak concentration Cmax, the more the color of each region R verges on white. The smaller the peak concentration Cmax, the more the color of each region R verges on the black. Although the differences between the concentrations of the regions R are shown only in three stages (white, gray and black) for convenience of description in FIG. 6A, the differences are actually shown in smaller multistage form.

The differences in magnitude of the peak concentration achieved times TTP related to the regions R lying in the slice Sx are shown in FIG. 6B in the form of shadings of the regions R. The larger the peak concentration achieved time TTP, the more the color of each region R verges on white. The larger the peak concentration achieved time TTP, the more the color of each region R verges on black. The differences between the concentrations of the regions R are shown in three stages (white, gray and black) for convenience of description in FIG. 6B in a manner similar to FIG. 6A.

The differences in magnitude of the post-bolus passage concentrations Cp related to the regions R lying in the slice Sx are shown in FIG. 6C in the form of shadings of the regions R. The larger the post-bolus passage concentration Cp, the more the color of each region R verges on the white. The smaller the post-bolus passage concentration Cp, the more the color of each region R verges on black. The differences between the concentrations of the regions R are shown in three stages (white, gray and black) for convenience of description in FIG. 6C in a manner similar to FIGS. 6A and 6B.

Generating such maps as shown in FIGS. 6A-6C enables the understanding of the differences in peak concentration Cmax between the regions R in the slice Sx, the differences in peak concentration achieved time TTP therebetween and the differences in post-bolus passage concentration Cp therebetween. It is understood that since, for example, the color of each region Re is white at any of the maps shown in FIGS. 6A through 6C, the values of Cmax, TTP and Cp are large. On the other hand, it is understood that since the color of each Rf is gray at any of the maps shown in FIGS. 6A through 6C, the values of Cmax, TTP and Cp are smaller than those of Cmax, TTP and Cp in each region Re. Incidentally, although regions R different in concentration are shown even outside the head of the subject at the maps shown in FIGS. 6A-6C, they are noise that appear upon map generation.

Although the three maps (map of peak concentration Cmax, map of peak concentration achieved time TTP and map of post-bolus passage concentration Cp) about the slice Sx are shown in FIGS. 6A-6C, three maps (map of peak concentration Cmax, map of peak concentration achieved time TTP and post-bolus passage concentration Cp) are generated even at other slices in a manner similar to the slice Sx (refer to FIGS. 7A-7C).

FIGS. 7A, 7B, and 7C are figures schematically showing the three maps (map of peak concentration Cmax, map of peak concentration achieved time TTP and post-bolus passage concentration Cp) of the respective slices 51 through Sn.

As shown in FIGS. 7A-7C, the map of the peak concentration Cmax, the map of the peak concentration achieved time TTP and the map of the post-bolus passage concentration Cp are generated for each of the slices S1 through Sn at Step S4. After the generation of these maps, the processing flow proceeds to Step S5.

At Step S5, the joint histogram generation device 65 (refer to FIG. 1) generates a joint histogram for a peak concentration Cmax, a peak concentration achieved time TTp and a post-bolus passage concentration Cp, from the maps of the peak concentrations Cmax, the maps of the peak concentration achieved times TTP and the maps of the post-bolus passage concentrations Cp each map obtained for each of the slices S1 through Sn (refer to FIGS. 7A-7C).

FIG. 8 is a diagram schematically showing one example of a joint histogram.

A large number of dots (white circles) are shown in the joint histogram. Each of the dots represents a relationship of three characteristic amounts (Cmax, TTP and Cp) in each of the regions R lying in the slices S1 through Sn. For example, a dot De represents a relationship of three characteristic amounts (Cmax, TTP and Cp) in the region Re (refer to FIG. 6) lying in the slice Sx. A dot Df represents a relationship of three characteristic amounts (Cmax, TTP and Cp) in the region Rf (refer to FIG. 6) lying in the slice Sx. A dot D1 represents a relationship of three characteristic amounts (Cmax, TTP and Cp) in a region Rm lying in the slice S8. A dot D2 represents a relationship of three characteristic amounts (Cmax, TTP and Cp) in a region Rn lying in the slice S3.

Further, a dot D3 represents a relationship of three characteristic amounts (Cmax, TTP and Cp) in one region Ro lying in the slice S7 and a relationship of three characteristic amounts (Cmax, TTP and Cp) in one region Rp lying in the slice S3. When the relationships of the three characteristic amounts (Cmax, TTP and Cp) become identical even in the case of the different regions R, one dot represents the relationships of three characteristic amounts (Cmax, TTP and Cp) in the different regions R as in the case of the dot D3.

After the joint histogram has been generated as shown in FIG. 8, the processing flow proceeds to Step S6.

At Step S6, the region extraction unit 67 (refer to FIG. 1) extracts artery-containing regions R and vein-containing regions R from all regions R contained in the slices S1 through Sn. Each of the artery-containing regions R is extracted to calculate an arterial input function to be described later, and each of the vein-containing regions R is extracted to calculate a venous output function to be described later. However, the artery-containing regions R and the vein-containing regions R exist in the slices S1 through Sn in mixed form. Further, various regions R such as regions R containing brain tissues, regions R located outside the head 8a of the subject 8, etc. exist therein. Therefore, the region extraction unit 67 makes use of the joint histogram shown in FIG. 8 so as to be able to extract the artery-containing region R and vein-containing region R. A description will be made below of how the artery-containing and vein-containing regions R are extracted from all regions R of the slices S1 through Sn.

The region extraction unit 67 projects a joint histogram onto a Cmax-TTP surface.

Figure 9:
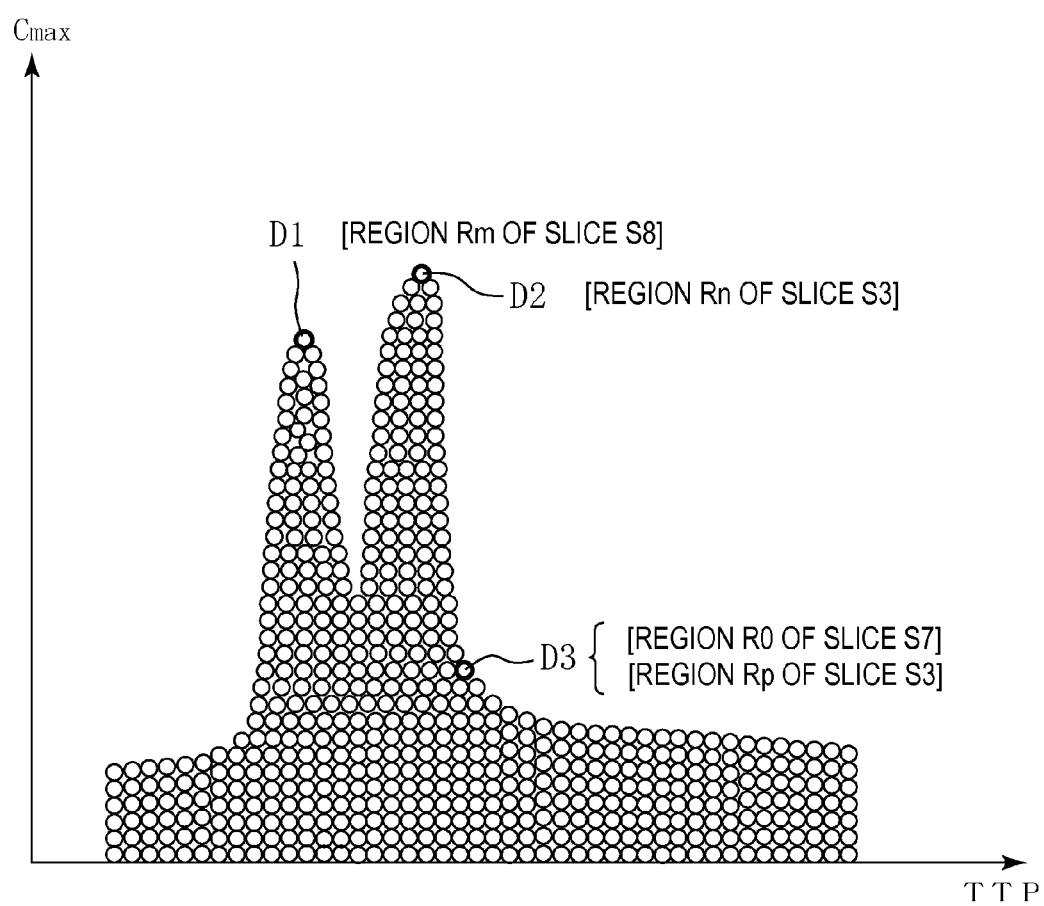
FIG. 9 is a two-dimensional profile obtained by projecting the joint histogram onto a Cmax-TTP surface.

FIG. 9 is a two-dimensional profile obtained by projecting the joint histogram onto the Cmax-TTP surface. The positions of plots D1, D2 and D3 are specifically shown in FIG. 9.

After such a two-dimensional profile as shown in FIG. 9 has been obtained, the region extraction unit 67 determines a profile or border line of the two-dimensional profile.

Figure 10:
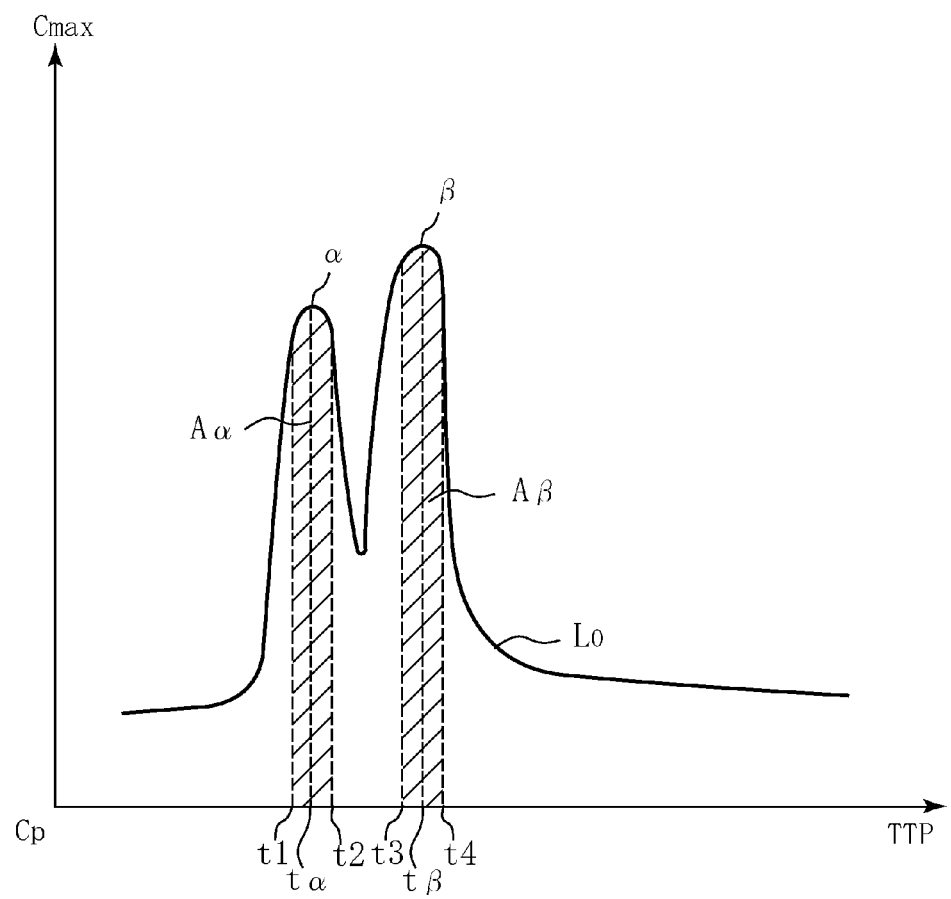
FIG. 10 is a diagram showing one example of a profile line of the two-dimensional profile shown in FIG. 9.

FIG. 10 is a diagram showing one example of the profile line of the two-dimensional profile shown in FIG. 9.

Two peaks α and β appear in the profile line Lo. A peak concentration achieved time tα of the peak α is shorter than a peak concentration achieved time tβ of the peak β. It is known that a peak concentration achieved time TTP of each artery-containing region R has a high possibility of appearing within a range from peak achieved times t1 to t2 about tα (time interval from t1 to t2 is 5 seconds or so, for example). Therefore, the region extraction unit 67 determines the range (hereinafter called "arterial range") from the peak achieved times t1 to t2 with respect to the joint histogram. It is also known that a peak concentration achieved time TTP of each vein-containing region R has a high possibility of appearing within a range from peak achieved times t3 to t4 about tβ (time interval from t3 to t4 is ten seconds or so, for example) about tβ. Therefore, the region extraction unit 67 determines the range (hereinafter called "venous range") Aβ from the peak achieved times t3 to t4 with respect to the joint histogram.

Figure 11:
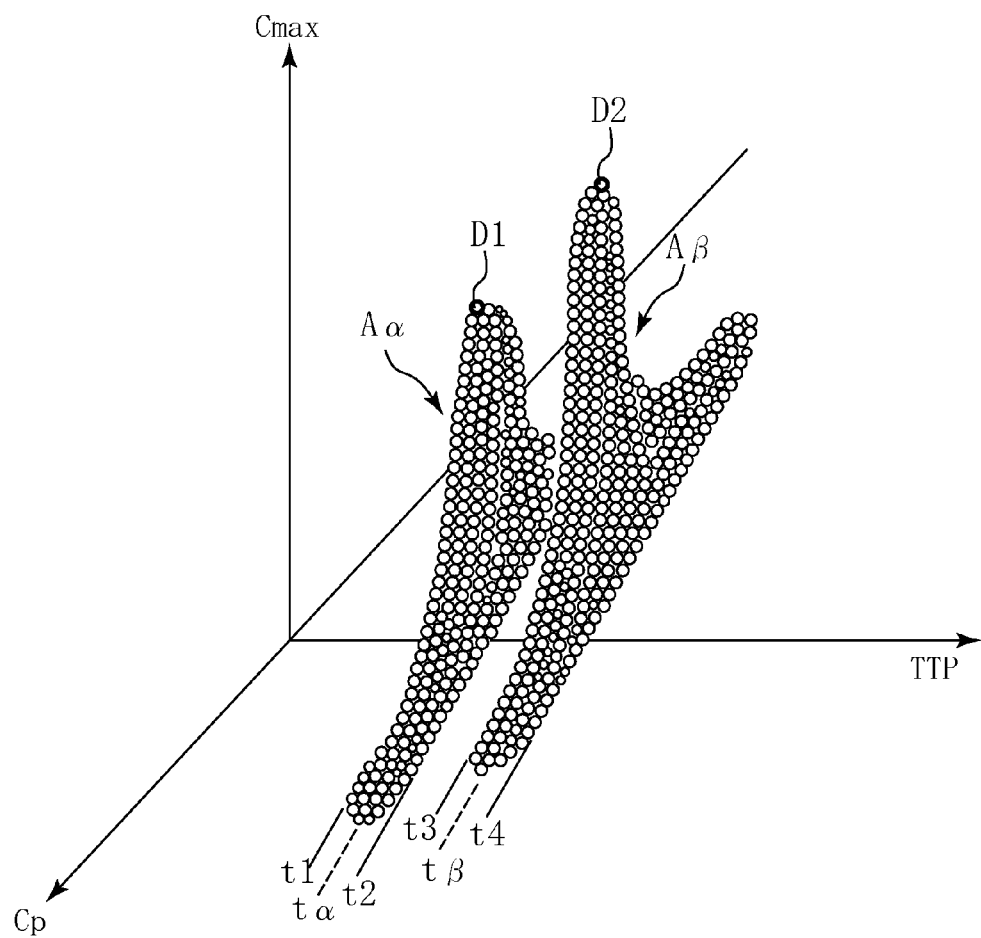
FIG. 11 is a diagram showing an arterial range Aα and a venous range Aβ determined with respect to the joint histogram.

FIG. 11 is a diagram showing the arterial range Aα and the venous range Aβ determined with respect to the joint histogram.

Each of dots contained in the arterial range Aα of the joint histogram represents a relationship of three characteristic amounts (Cmax, TTP and Cp) of each region R having the peak achieved time TTP from t1 to t2. On the other hand, each of dots contained in the venous range Aβ of the joint histogram represents a relationship of three characteristic amounts (Cmax, TTP and Cp) of each region R having the peak achieved time TTP from t3 to t4.

A description will next be made of to which region R in the slices S1 through Sn each of the dots contained in the arterial and venous ranges Aα and Aβ of the joint histogram corresponds, with reference to FIGS. 12A-12C.

FIG. 12A is a diagram of a projection of the arterial range Aα of the joint histogram shown in FIG. 11 onto the Cmax-Cp surface, FIG. 12B is a diagram of a projection of the venous range Aβ of the joint histogram shown in FIG. 11 onto the Cmax-Cp surface, and FIG. 12C is a diagram for showing whether each of the dots contained in the arterial and venous ranges Aα and Aβ of the joint histogram represents the characteristic amounts (Cmax, TTP and Cp) of any of the regions R lying in the slices S1 through Sn.

Only the sections of four slices S1, S3, Sn-4 and Sn-1 of the slices S1 through Sn are shown in FIG. 12C for convenience of explanation. The dots contained in the arterial range Aα (refer to FIG. 12A) of the joint histogram respectively represent characteristic amounts (Cmax, TTP and Cp) of regions R1 or R2 indicated by black circles lying in the slices S1, S3, Sn-4 and Sn-1. Each region R1 is a region lying inside the head 8a of the subject, and each region R2 is a region lying outside the head 8a of the subject. On the other hand, the dots contained in the venous range Aβ (refer to FIG. 12B) of the joint histogram respectively represent characteristic amounts (Cmax, TTP and Cp) of regions R3 or R4 indicated by "X" lying in the slices S1, S3, Sn-4 and Sn-1. Each region R3 is a region lying inside the head 8a of the subject, and each region R4 is a region lying outside the head 8a of the subject.

While the regions R1 through R4 are shown only with respect to the four slices S1, S3, Sn-4 and Sn-1 of the slices S1 through Sn in FIG. 12C, other slices also have the regions R1 through R4 in a manner similar to the slices S1, S3, Sn-4 and Sn-1.

The region extraction unit 67 extracts the regions R1 through R4 from within all the regions R of the slices S1 through Sn.

It is however known that referring to the slices S1, S3, Sn-4 and Sn-1 of FIG. 12C, the regions R2 and R4 exist even outside the head 8a of the subject 8. Since the regions R2 and R4 are of regions lying outside the head 8a of the subject 8, they do not correspond to not only the artery-containing regions R1 but also the vein-containing regions R3 apparently. Thus, the regions R2 and R4 are noise that cannot be used for the calculation of the arterial input function and the venous output function. Therefore, the processing flow proceeds to Step S7 to eliminate the regions R2 and R4 brought to noise.

At Step S7, the noise elimination unit 68 (refer to FIG. 1) eliminates dots each corresponding to each region R2 from the arterial range Aα of the joint histogram and eliminates dots each corresponding to each region R4 from the venous range Aβ of the joint histogram. The noise elimination unit 68 first detects dots indicative of the characteristic amounts (Cmax, TTP and Cp) of the regions R2 and R4 from the artery and venous ranges Aα and Aβ of the joint histogram, in order to eliminate the dots corresponding to the regions R2 and R4. In the present embodiment, the noise elimination unit 68 detects dots (refer to FIG. 12A) contained in some ranges N1 through N4 lying in the arterial range Aα of the joint histogram as the dots each indicative of the characteristic amounts (Cmax, TTP and Cp) of each region R2. Further, the noise elimination unit 68 detects dots (refer to FIG. 12B) contained in some ranges N5 through N7 lying in the venous range Aβ of the joint histogram as the dots each indicative of the characteristic amounts (Cmax, TTP and Cp) of each region R4.

After the dots contained in the ranges N1 through N7 of the joint histogram have been detected as mentioned above, the noise elimination unit 68 eliminates the dots contained in the ranges N1 through N7 of the joint histogram.

FIGS. 13A, 13B, and 13C are diagrams showing the manner after the dots are eliminated from the ranges N1 through N7 of the joint histogram.

FIG. 13A is a diagram of projections of the dots left in the arterial range Aα of the joint histogram after the elimination of the dots onto the Cmax-Cp surface, FIG. 13B is a diagram of projections of the dots left in the venous range Aβ of the joint histogram after the elimination of the dots onto the Cmax-Cp surface, and FIG. 13C is a diagram for showing whether each of the dots left in the arterial and venous ranges Aα and Aβ of the joint histogram represents the characteristic amounts (Cmax, TTP and Cp) of any of the regions R lying in the slices S1 through Sn.

It is understood that referring to FIG. 13A, the dots having existed in the ranges N1 through N4 of the joint histogram have been removed. It is understood that with the elimination of the dots having existed in the ranges N1 through N4 of the joint histogram, each region R (refer to FIGS. 12A-12C) extracted at Step S6 is left only inside the head 8a of the subject 8.

After the dots taken as noise have been eliminated, the processing flow proceeds to Step S8.

At Step S8, the region selection unit 69 (refer to FIG. 1) narrows down the corresponding regions R1 and R3 used to determine the arterial input function and the venous output function from within the regions R1 and R3 left within the head 8a of the subject 8 in the slices S1 through Sn. It is desirable that the region R1 used to determine the arterial input function is as large as possible in Cmax. It is desirable that the region R3 used to determine the venous output function is also as large as possible in Cmax. Therefore, the region selection unit 69 selects regions each large in Cmax from within the regions R1 and R3 left within the head 8a of the subject 8 in the slices S1 through Sn.

FIGS. 14A, 14B, and 14C are diagrams showing which region R is selected from within the regions R left in the head 8a of the subject 8 with the slices S1 through Sn set thereto.

In the present embodiment, the region selection unit 69 selects three dots D11, D12 and D13 in order of increasing peak concentration Cmax from the arterial range Aβ of the joint histogram as shown in FIG. 14A. When the dots are selected from the arterial range Aα of the joint histogram are selected, the three dots D11, D12 and D13 are selected in increasing order of peak concentration Cmax regardless of whether the post-bolus passage concentration Cp is of a positive or negative value. The dots D11, D12 and D13 respectively represent characteristic amounts (Cmax, TTP and Cp) of a region R11 of the slice S3, a region R12 of the slice Sn-4 and a region 13 of the slice Sn-1. Contrast agent concentration-time curves C11, C12 and C13 of the respective regions R11, R12 and R13 are schematically shown in FIG. 14C.

When the dots are selected from the arterial range Aα of the joint histogram as described above, the three dots D11, D12 and D13 are selected in order of increasing peak concentration Cmax regardless of whether the post-bolus passage concentration Cp is of the positive or negative value. However, three dots D21, D22 and D23 are selected in increasing order of Cmax from within dots at each of which the post-bolus passage concentration Cp has a negative value, without selecting a dot Dn at which the post-bolus passage concentration Cp has a positive value, from the venous range Aβ of the joint histogram. This reason will be explained below.

Figures 15A, 15B:
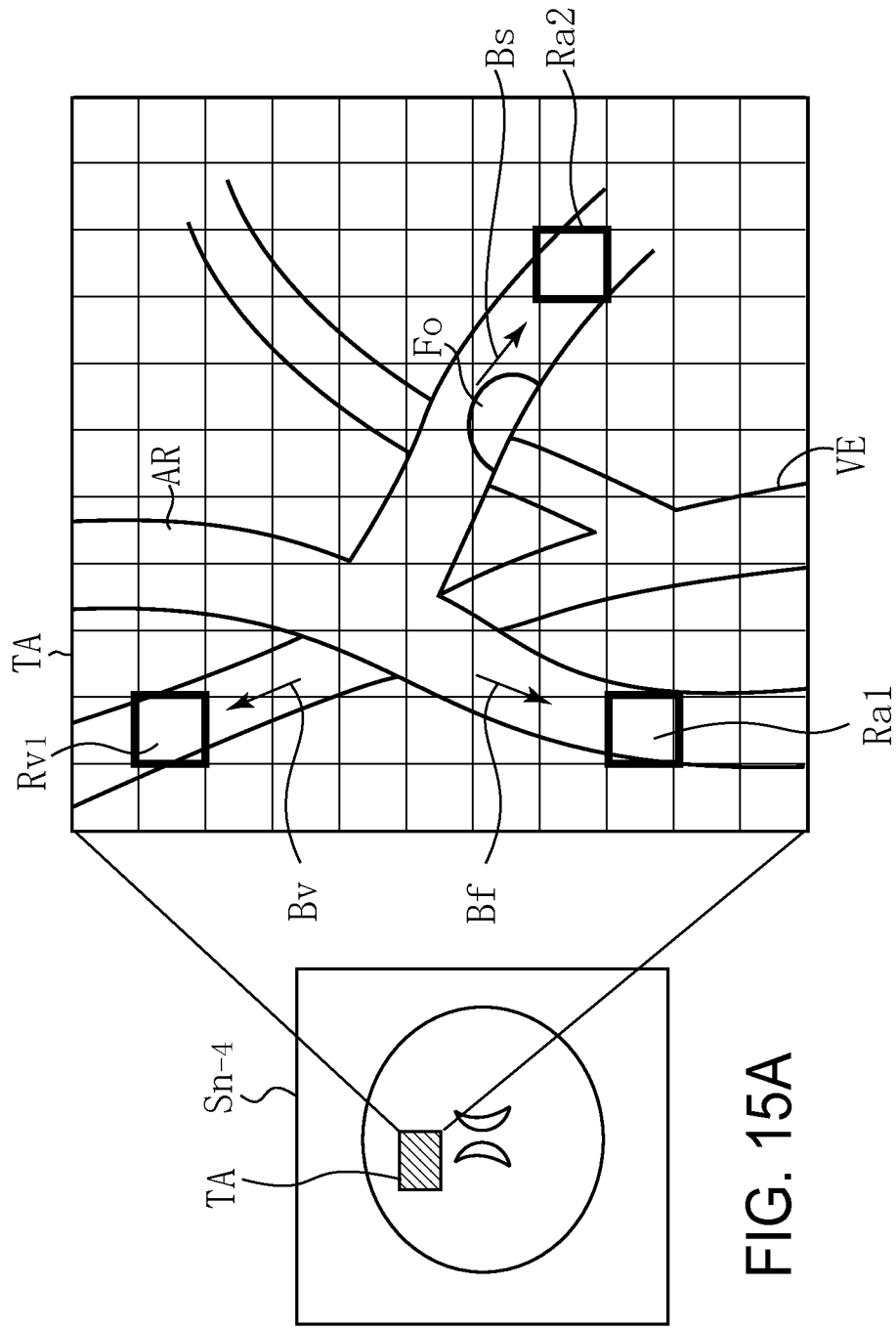
FIGS. 15A and 15B are diagrams showing the reason that each dot at which a concentration Cp after passage of a bolus has a positive value, is not selected from the venous range Aβ of the joint histogram.

FIGS. 15A and 15B are diagrams showing the reason that the dot at which the post-bolus passage concentration Cp has the positive value is not selected from the venous range Aβ of the joint histogram.

FIG. 15A is a diagram showing a partial target or region TA in the head 8a, of the slice Sn-4, and FIG. 15B is an enlarged view of the partial target TA.

An artery AR and a vein VE are shown in the target TA. Arterial blood Bf flows into a region Ra1 of the artery AR. The region Ra1 in which the arterial blood Bf flows normally has a characteristic at which a peak concentration Cmax first appears rather than a region Rv1 in which venous blood Bv flows (refer to FIGS. 5B and 5C).

When, however, a focus FO exists in the artery AR of the target TA and the inside diameter of the artery AR becomes narrow, arterial blood Bs that flows through the focus FO becomes slower than the arterial blood Bf. Hence, the arterial blood Bs slow in blood flow flows into a region Ra2. Thus, the time at which a peak concentration Cmax of the region Ra2 appears becomes slower than the time at which the peak concentration Cmax of the region Ra1 appears. As a result, the time at which the peak concentration Cmax of the region Ra2 becomes close to the time at which Cmax of the vein-containing region Rv1 appears. Thus, even though only the peak concentration Cmax of the region Ra2 is examined, it is not possible to make a distinction whether the region Ra2 is of either the artery-containing region or the vein-containing region.

However, it is generally known that there is a tendency that the post-bolus passage concentration Cp is calculated as a positive value in each of the artery-containing regions Ra1 and Ra2, whereas there is a tendency that the post-bolus passage concentration Cp is calculated as a negative value in the vein-containing region Rv1 (refer to FIGS. 5B and 5C). Thus, although the dot Dn at which the post-bolus passage concentration Cp has the positive value is contained in the venous range Aβ of the joint histogram referring to FIG. 14B, the dot Dn has a possibility of being an artery-containing pixel Ra2 (refer to FIG. 15B). Therefore, the region selection unit 69 selects three dots D21, D22 and D23 in increasing order of peak concentration Cmax from the dots at each of which the post-bolus passage concentration Cp has the negative value, in the venous range Aβ of the joint histogram. The dots D21, D22 and D23 respectively represent characteristic amounts (Cmax, TTP and Cp) of a region R21 of the slice S1, a region R22 of the slice S3 and a region R23 of the slice Sn-4. Contrast agent concentration-time curves C21, C22 and C23 of the regions R21, R22 and R23 are schematically shown in FIG. 14C.

Thus, the regions R11, R12, R13, R21, R22 and R23 are selected from the regions R1 and R3 left within the head 8a of the subject 8 at the slices S1 through Sn in this way.

After the selection of the regions R11, R12, R13, R21, R22 and R23, the processing flow proceeds to Step S9.

At Step S9, the function calculation device 70 (refer to FIG. 1) adds and averages the contrast agent concentration-time curves C11, C12 and C13 of the selected three regions R11, R12 and R13 thereby to calculate the corresponding arterial input function. Further, the function calculation device 70 adds and averages the contrast agent concentration-time curves C21, C22 and C23 of the selected three regions R21, R22 and R23 thereby to calculate the corresponding venous output function.

FIG. 16 is a diagram showing the calculated arterial input and venous output functions.

After the arterial input function Fa and the venous output function Fv have been calculated, the program is completed.

In the present embodiment, the regions R21, R22 and R23 used to calculate the venous output function Fv are selected from the slices S1 through Sn by selecting the three dots in increasing order of Cmax from within the dots at each of which the peak concentration Cp has the negative value. Thus, the artery-containing region Ra2 (refer to FIG. 15B) can be prevented from being contained in the regions R21, R22 and R23, thereby making it possible to calculate a more accurate venous output function Fv.

Incidentally, although the contrast agent concentration-time curves C21, C22 and C23 (refer to FIG. 14C) of the three regions R21, R22 and R23 are added and averaged to calculate the arterial input function Fa and the venous output function Fv in the present embodiment, the arterial input function Fa and the venous output function Fv may be calculated using contrast agent concentration-curves of one region, two regions or four or more regions. Although the contrast agent concentration-curves are added and averaged thereby to calculate the arterial input function Fa and the venous output function Fv in the present embodiment, the arterial input function Fa and the venous output function Fv may be calculated by a method other than the adding/averaging of the contrast agent concentration-curves.

In the present embodiment, the three characteristic amounts (peak concentration Cmax, peak concentration achieved time TTP and post-bolus passage concentration Cp) have been calculated as the characteristic amounts of the contrast agent concentration-time curves Ga and Gv (refer to FIGS. 5B and 5C). If, however, the calculated characteristic amounts are of characteristic amounts useful in distinguishing between the artery-containing region and the vein-containing region, then other characteristic amounts can also be used.

In the present embodiment, the noise elimination unit 68 eliminates each region taken as noise after the regions have been extracted from the slices S1 through Sn by the region extraction unit 67. However, the regions may be eliminated before the extraction of the regions from the slices S1 through Sn by the region extraction unit 67.

In the present embodiment, the MRI system 1 (refer to FIG. 1) calculates the arterial input function Fa and the venous output function Fv, based on the data of the images acquired from the subject 8. However, the calculation of the arterial input function Fa and the venous output function Fv may be conducted by another system for calculating the arterial input function Fa and the venous output function Fv, other than the MRI system.

Further, although the blood flow dynamics of the head 8a of the subject 8 are analyzed in the present embodiment, the invention is applicable even to the analysis of other target or region other than the head 8a.

Many widely different embodiments of the invention may be configured without departing from the spirit and the scope of the present invention. It should be understood that the present invention is not limited to the specific embodiments described in the specification, except as defined in the appended claims.

What is claimed is:

1. A blood flow dynamic analysis apparatus configured to acquire data from a plurality of regions lying in slices set to a subject with a contrast agent injected therein and to analyze blood flow dynamics of the subject based on the data, said blood flow dynamic analysis apparatus comprising:
    a contrast agent concentration profile generation device configured to generate a profile indicative of a temporal change in a concentration of the contrast agent for each of the regions;
    a characteristic amount calculation device configured to calculate the concentration of the contrast agent in each region as contrast agent passes through the region based on a respective profile;
    a graphical representation generation device configured to generate a graphical representation containing a cluster of dots representing the concentration of the contrast agent in each region as the contrast agent passes through the region;
    a region determination device configured to determine a region of the plurality of regions in which a vein exists based on the graphical representation; and
    a function calculation device configured to calculate a venous output function, based on the temporal change in the concentration of the contrast agent in the region in which the vein exists.

2. The blood flow dynamic analysis apparatus according to claim 1, wherein said characteristic amount calculation device is configured to calculate a peak concentration at which the concentration of the contrast agent reaches a peak, and a peak concentration achieved time necessary for the concentration of the contrast agent to reach the peak concentration, from each of the contrast agent concentration profiles.

3. The blood flow dynamic analysis apparatus according to claim 2, wherein the cluster of dots represents at least the peak concentration and the peak concentration achieved time in each region.

4. The blood flow dynamic analysis apparatus according to claim 3, wherein said region determination device comprises:
    a region extraction unit configured to extract a plurality of first regions each having a peak concentration achieved time lying in a first range based on the graphical representation;
    a noise elimination unit configured to eliminate regions determined by the noise elimination unit to be noise from within the first regions; and
    a region selection unit configured to select a region in which a vein exists, from the first regions with the noise eliminated therefrom, based on the concentration of the contrast agent in each of the regions as the contrast agent passes through the region.

5. The blood flow dynamic analysis apparatus according to claim 4, wherein said region selection unit is configured to select the region in which the vein exists, from the first regions with the noise eliminated therefrom, based on the peak concentration in each of the first regions and the concentration of the contrast agent in each of the first regions as the contrast agent passes through the region.

6. The blood flow dynamic analysis apparatus according to claim 4, wherein:
    said region extraction unit is configured to extract a plurality of second regions each having a peak concentration achieved time lying in a second range from the regions, based on the graphical representation;
    said noise elimination unit is configured to extract regions determined by the noise elimination unit to be noise from the second regions; and
    said region selection unit is configured to select a region in which an artery exists, from the second regions with the regions determined to be noise eliminated therefrom, based on the peak concentration in each of the second regions.

7. The blood flow dynamic analysis apparatus according to claim 5, wherein:
    said region extraction unit is configured to extract a plurality of second regions each having a peak concentration achieved time lying in a second range from the regions, based on the graphical representation;
    said noise elimination unit is configured to eliminate regions determined by the noise elimination unit to be noise from the second regions; and
    said region selection unit is configured to select a region in which an artery exists, from the second regions with the regions determined to be noise eliminated therefrom, based on the peak concentration in each of the second regions.

8. The blood flow dynamic analysis apparatus according to of claim 1, wherein said characteristic amount calculation device is configured to calculate the concentration of the contrast agent in each of the regions as the contrast agent passes through the region, based on the concentration of the contrast agent after a predetermined time has elapsed from a time at which the concentration of the contrast agent has reached a peak.

9. The blood flow dynamic analysis apparatus according to claim 8, wherein the predetermined time is a time ranging from 5 to 10 seconds.

10. The blood flow dynamic analysis apparatus according to claim 1, wherein the data are data acquired by a magnetic resonance imaging system.

11. A magnetic resonance imaging system comprising:
a contrast injection device configured to inject a contrast agent into a subject; and
a blood flow dynamic analysis apparatus configured to acquire data from a plurality of regions lying in slices set to the subject with a contrast agent injected therein and to analyze blood flow dynamics of the subject based on the data, wherein said blood flow dynamic analysis apparatus comprises:
a contrast agent concentration profile generation device configured to generate a profile indicative of a temporal change in a concentration of the contrast agent for each of the regions;
a characteristic amount calculation device configured to calculate the concentration of the contrast agent in each region as a contrast agent passes through the region based on a respective profile;
a graphical representation generation device configured to generate a graphical representation containing a cluster of dots representing the concentration of the contrast agent in each region as the contrast agent passes through the region;
a region determination device configured to determine a region of the plurality of regions in which a vein exists based on the graphical representation; and
a function calculation device configured to calculate a venous output function, based on the temporal change in the concentration of the contrast agent in the region in which the vein exists.

12. A method of a blood flow dynamic analysis for acquiring data from a plurality of regions lying in slices set to a subject with a contrast agent injected therein and analyzing blood flow dynamics of the subject, based on the data, said method comprising:
generating, by a profile generation device, profiles each indicative of a temporal change in the concentration of contrast agent for every region lying in the slices;
calculating a concentration of the contrast agent in each of the regions as a contrast agent passes through the regions, from the profiles;
generating, by a graphical representation generation device, a graphical representation containing a cluster of dots that represent a relationship of three characteristic amounts of the concentration of the contrast agent in the regions as the contrast agent passes through the regions;
determining, by a region extraction unit, a region in which a vein exists, from the regions, based on the graphical representation; and
calculating, by the region extraction unit, a venous output function, based on a temporal change in the concentration of the contrast agent in the region in which the vein exists.

13. The magnetic resonance imaging system according to claim 11, wherein said characteristic amount calculation device is configured to calculate a peak concentration at which the concentration of the contrast agent reaches a peak, and a peak concentration achieved time necessary for the concentration of the contrast agent to reach the peak concentration, from each of the contrast agent concentration profiles.

14. The magnetic resonance imaging system according to claim 13, wherein the cluster of dots represents at least the peak concentration and the peak concentration achieved time in each region.

15. The magnetic resonance imaging system according to claim 14, wherein said region determination device comprises:
a region extraction unit configured to extract a plurality of first regions each having a peak concentration achieved time lying in a first range based on the graphical representation;
a noise elimination unit configured to eliminate regions determined by the noise elimination unit to be noise from within the first regions; and
a region selection unit configured to select the region in which a vein exists, from the first regions with the noise eliminated therefrom, based on the concentration of the contrast agent in each of the regions as the contrast agent passes through the region.

16. The magnetic resonance imaging system according to claim 15, wherein said region selection unit is configured to select the region in which the vein exists, from the first regions with the noise eliminated therefrom, based on the peak concentration and the concentration of the contrast agent in each of the first regions as the contrast agent passes through the region.

17. The magnetic resonance imaging system according to claim 15, wherein:
said region extraction unit is configured to extract a plurality of second regions each having a peak concentration achieved time lying in a second range from the regions, based on the graphical representation;
said noise elimination unit is configured to extract regions determined by the noise elimination unit to be noise from the second regions; and
said region selection unit is configured to select a region in which an artery exists, from the second regions with the regions determined to be noise eliminated therefrom, based on the peak concentration in each of the second regions.

18. The magnetic resonance imaging system according to claim 16, wherein:
said region extraction unit is configured to extract a plurality of second regions each having a peak concentration achieved time lying in a second range from the regions, based on the graphical representation;
said noise elimination unit is configured to eliminate regions determined by the noise elimination unit to be noise from the second regions; and
said region selection unit is configured to select a region in which an artery exists, from the second regions with the regions determined to be noise eliminated therefrom, based on the peak concentration of the contrast agent.

19. The magnetic resonance imaging system according to of claim 11, wherein said characteristic amount calculation device is configured to calculate the concentration of the contrast agent in each of the regions as the contrast agent passes through the region, based on the concentration of the contrast agent after a predetermined time has elapsed from a time at which the concentration of the contrast agent has reached a peak.

20. The magnetic resonance imaging system according to claim 19, wherein the predetermined time is a time ranging from 5 to 10 seconds.

* * * * *